United States Patent [19]

Ferber et al.

[11] 4,440,966

[45] Apr. 3, 1984

[54] PRODUCTION OF INDANES

[75] Inventors: Gerald J. Ferber, Ilford; Peter J. Goddard, Luton, both of England

[73] Assignee: Bush Boake Allen, London, England

[21] Appl. No.: 357,189

[22] Filed: Mar. 11, 1982

[30] Foreign Application Priority Data

Mar. 13, 1981 [GB] United Kingdom ............... 8108050

[51] Int. Cl.$^3$ ............... C07C 3/00; C07C 3/50; C07C 3/54
[52] U.S. Cl. ............... 585/415; 585/25; 585/27; 585/466
[58] Field of Search ............... 585/24, 27, 410, 415, 585/25, 436, 466

[56] References Cited

U.S. PATENT DOCUMENTS

| 2,851,501 | 9/1958 | Benz et al. | 585/410 |
| 3,151,174 | 9/1964 | Wood et al. | 585/27 |
| 3,347,946 | 10/1967 | Wood et al. | 585/27 |
| 4,308,412 | 12/1981 | Wiegers et al. | 585/410 |

FOREIGN PATENT DOCUMENTS

| 49-1059846 | 11/1974 | Japan | 585/27 |
| 796129 | 6/1958 | United Kingdom | 585/27 |
| 796130 | 6/1958 | United Kingdom | 585/27 |

Primary Examiner—Delbert E. Gantz
Assistant Examiner—A. Pal
Attorney, Agent, or Firm—Kane, Dalsimer, Kane, Sullivan and Kurucz

[57] ABSTRACT

The reaction between particular styrenes and particular alkenes to produce alkyl substituted indanes has been discovered to give improved yields when phosphoric acid is used as the catalyst. The catalyst is readily separated from the organic products at the end of the reaction and can be used repeatedly to catalyze further reactions. The product further comprises novel adducts of the alkene and styrene which are converted into the desired isochroman products when the indanes are used as intermediates in the production of isochromans.

17 Claims, No Drawings

PRODUCTION OF INDANES

This invention relates to a novel process for the production of polyalkyl indanes which are useful as intermediates in the synthesis of a variety of valuable organic chemicals. They find particular application as intermediates in the production of a variety of polycylic compounds which are useful as ingredients of compounded perfumery compositions.

U.S. Pat. No. 2,851,501 describes the utility of polyalkyl indanes having the formula:

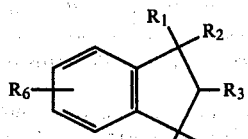

wherein $R_{1-6}$ represent hydrogen atoms or alkyl groups comprising 1 to 3 carbon atoms as intermediates in chemical synthesis.

A convenient method for the production of these indanes is the reaction between a styrene and an alkene in the presence of an acid catalyst such as is described in U.S. Pat. No. 2,851,501 and British Pat. No. 991,146. U.S. Pat. No. 2,851,501 states that the reaction should be carried out in the presence of a catalyst which is an acid acting catalyst. Specific catalysts which are suggested as being useful are sulphuric acid and phosphoric acid (as aqueous solutions having concentration of 70 to 85% acid or in the presence of monobasic organic acids having from 1 to 3 carbon atoms such as formic acid, propionic acid, chlorosubstituted acetic acid etc.), boron trifluoride, zinc chloride and their complexes such as their etherates or mixtures of any one of these with monobasic organic acids having from 1 to 3 carbon atoms and monobasic organic acids having a dissociation constant of $1.76 \times 10^{-4}$ or more such as formic acid and halogenated acetic acids. The processes exemplified in this patent employ a mixture of sulphuric acid with acetic acid as the catalyst in all of the examples except one in which a complex of boron trifluoride and methyl ether is used. The use of an organic acid with the sulphuric acid promotes mutual solubility between the acid and organic phases in a two phase system. This mutual solubility leads to some organic acid being dissolved in the organic phase at the end of the reaction. This is disadvantageous in that this dissolved acid has to be washed out from the organic product and organic acid content of the catalyst system must be replenished.

The organic reaction product is a mixture comprising the desired indanes and dimeric products derived from the alkene and styrene in varying proportions. The formation of the dimeric products derived from the alkene and the styrene as well as other by-product materials reduces the yield of the desired indanes and is thereby disadvantageous.

We have now discovered that the yield of indanes and useful by-products obtained by the reaction of particular styrenes with particular alkenes can be increased by using phosphoric acid as the catalyst for the reaction. The phosphoric acid readily separates virtually completely from the organic phase at the end of the reaction and can be recovered and recycled with a high degree of efficiency.

From one aspect our invention provides:

A process for the production of an indane of the formula:

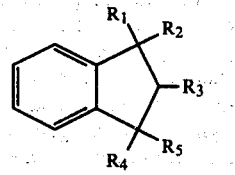

wherein $R_3$ represents a hydrogen atom or a methyl group; at least one of $R_1$ and $R_2$ represents a methyl group and the other represents a hydrogen atom or a methyl group and $R_4$ and $R_5$, which may be the same or different, represent alkyl groups having from 1 to 3 carbon atoms which comprises reacting a styrene with an alkene in the presence of an acid catalyst characterised in that the styrene is a compound of the formula I:

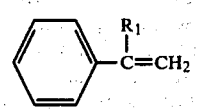

wherein $R_1$ represents a hydrogen atom or a methyl group; the alkene is selected from the group the group consisting of propylene, 2 methyl but-1-ene, 2 methyl but-2-ene, 2-methyl pent-1-ene, 2 methyl pent-2-ene, 3 methyl but-1-ene isobutylene and di-isobutylene and the acid catalyst is phosphoric acid.

The novel processes of our invention may also be carried out utilising an alcohol as the reactant in place of the alkene, the alcohol being such that it is capable of being dehydrated to form alkenes under the conditions employed for the reaction. Examples of alcohols which may be employed are tertiary amyl alcohol (which acts as a precursor of 2 methyl-but-2-ene and 2 methyl but-1-ene) and 2-methyl propan-1-ol, 2 methyl propan 2-ol, secondary amyl alcohol, tertiary methyl pentanol and 2-methyl-pentan-3-ol.

The phosphoric acid may contain minor quantities e.g. less than 20% of the acid content of other acids, but preferably no other acid is present.

The phosphoric acid catalyst is preferably employed in the form of an aqueous solution thereof containing at least 85% by weight of phosphoric acid. More preferably a solution containing from 85 to 95% or most preferably 88 to 92% by weight of phosphoric acid is employed. The quantity of phosphoric acid which is employed may vary through a wide range but preferably a quantity of from 1.0 to 3.0 or most preferably about 1.25 to 2.0 moles of acid per mole of alkene reactant are employed.

The reaction can conveniently be carried out by reacting substantially equimolar quantities of styrene and alkene. Preferably the quantity of the styrene is least equal to the quantity of alkene and it may be employed in excess quantities e.g. up to 3.0 moles of styrene per moles of alkene.

The reaction may conveniently be carried out by the gradual addition of a mixture of the styrene and alkene reactants to the catalyst in an appropriate reaction vessel. The temperature of the reaction medium is preferably maintained within the range 0° to 50° C. or more preferably in the range 25° to 35° C., most preferably 25° to 30° C. The phosphoric acid may be a liquid phase, a supercooled liquid or a slurry of phosphoric acid crystals in a liquid phase depending upon the concentration of acid used and the temperature employed. The reaction medium is usually stirred in order to ensure thorough mixing, and preferably sufficiently strongly to achieve the formation of of a meta-stable-emulsion. It may be advantageous to add a small quantity e.g. 1 or 2% of an emulsifying agent or agents (usually a cationic or non-ionic emulsifying agent) to the reaction medium in order to encourage the formation of such an emulsion. The quantity of any such additive should be carefully controlled so as to avoid the formation of a stable emulsion at the end of the reaction thereby allowing the acid and organic phases to separate. The presence of impurities in the reactants, especially the styrene, may prevent the formation of a meta-stable emulsion during the reaction and it may be preferable to purify the reactants e.g. by fractional distillation prior to the reaction.

The rate of addition of the reactants is adjusted so as to help maintain the temperature of the reaction medium within the desired range. Normally the addition will be completed within a period of from 2 to 6 hours. Thereafter the reaction medium is stirred to a period of up to 2 hours in order to ensure complete reaction.

The reaction is preferably carried out in the absence of a solvent although an inert solvent may be added if desired. Aliphatic hydrocarbons and chlorinated hydrocarbons may be employed as solvents.

The reaction product rapidly settles into an acid layer and an organic layer which may separated. The acid layer comprises the catalyst and may be recycled for use with another reaction batch. A further advantage of this invention is that the separated acid can be repeatedly recycled without losing its efficacy or contaminating the product in any way. Also the acid is recovered in almost quantitative amounts (99%) even after repeated recycling, whereas when mixtures of sulphuric and an organic acid are used significant quantities (5%) of the acid separate into the organic phase and are lost during the purification thereof.

The separated organic phase is conveniently worked up e.g. by washing with dilute alkali and water. The components thereof can be separated by fractional distillation. In general three main product fractions can be identified. The lowest boiling comprises the dimeric materials formed from the alkene, the second (boiling at 70°–110° C. at 6 mm Hg) the indanes and precursors thereof and the highest boiling the dimeric materials formed from the styrene.

The most valuable fraction is the second. It will usually comprise a mixture of at least two indanes even when the process has been carried out using a single styrene and a single alkene. The use of mixtures of alkenes or styrenes as starting material(s) usually leads to the formation of a product containing a more complex mixture of indanes.

The second products fraction may be separated into its component chemicals but, more usually, where the indanes are for use as a chemical intermediate, this product is used directly without any separation.

The products of the processes of our invention find particular application as intermediates in the synthesis of certain isochromans such as are described in British Pat. No. 991146 and which find use as ingredients of compounded perfumery composition. They may therefore be reacted with an alkylene oxide in the presence of an electrophilic catalyst and subsequently with formaldehyde to yield such isochromans using the techniques described in the aforesaid British Pat. No. 991146 or those described in British Pat. Nos. 1219046, 1452049 and 1524076 and European Patent Application 0004914. The use of the mixture of compounds obtained leads to the production of a mixture of isochromans which mixture has an attractive odour and may be used as an ingredient of compounded perfumery compositions. We have discovered that in the course of this synthesis of the isochromans from the indanes which form part of the second product fraction certain of the other components of that product fraction are converted to the desired isochromans. Thus procedures using the unseparated second product fraction obtained by fractional distillation represent a preferred aspect of our invention.

The preferred indane products of our invention are those having the aforesaid formula wherein both $R_1$ and $R_2$ represents methyl groups, the most preferred being those wherein both $R_4$ and $R_5$ also represent methyl groups. The most preferred indane is the compound having the aforesaid formula wherein $R_3$ represents a methyl group.

The most preferred styrene for present use is methyl styrene i.e. the compound of the above formula wherein $R_1$ represents a methyl group. The preferred alkenes for present use are 2-methyl-but-1-ene, 2 methyl-but-2-ene and isobutylene.

The processes of our invention find particular application to the reaction between -methyl styrene and a 2-methyl butene, especially 2 methyl-2-butene (or tertiary amyl alcohol). Such a process is preferably carried out by adding equimolar quantities of the reactants to from 1.0 to 5.0 moles preferably from 1.0 to 3.0 or most preferably 1.5 to 2.0 moles of 90% w/w phosphoric acid and maintaining the reaction medium at the temperature of from 0° to 50° C. or more preferably form 25° to 30° C. The product of such a reaction has been found to comprise a mixture of the indane having the formula:

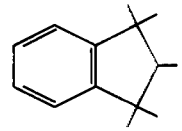

i.e. wherein $R_1$, $R_2$, $R_3$ and $R_4$ and $R_5$ represent methyl groups which compound is commonly termed pentamethylindan and an indane having the formula:

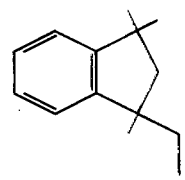

i.e. wherein $R_1$, $R_2$ and $R_4$ represents methyl groups and $R_5$ represents an ethyl group and $R_3$ represents a hydrogen atom which is (1,1,3-trimethyl-3-ethyl) indane.

The product of this reaction has been discovered to comprise at least two chemicals which are adducts of the butenes and styrene which are useful as intermediates in the synthesis of isochromans by virtue of the fact that they appear to cyclise to form indanes and subsequently to be converted to isochromans. The compounds in question are 2,3,4 trimethyl-4-penyl-pent-1-ene and 2,4 dimethyl-2-phenyl hex-4-ene (cis and trans isomers thereof) i.e. the compounds having the formulae:

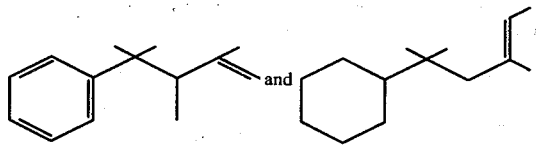

These compounds are believed to be novel and constitute another aspect of our invention.

Similarly mixtures of pentamethyl indane and (1,1,3 trimethyl 3 ethyl) indane are believed to be novel and constitute another aspect of our invention.

The invention is illustrated by the following examples:

EXAMPLE 1

A mixture of -methylstyrene[1] (345, 3 moles) and commercial grade 2-methylbut-2-ene[2] containing 85% 2-methylbut-2-ene, 8% 2 methylbut-1-ene and 7% $C_5$ alkanes (210 g, 3 moles) was added over 3.75 hours to 90% w/w ortho phosphoric acid (519 g, 4.8 moles as 100% phosphoric acid)[3] at 25°–27° C. Stirring was continued for a further 2 hours. The mixture was allowed to separate when 511 g of the acid was recovered. The organic layer was washed successively with water (75 g), 5% sodium hydroxide solution (205 g) and water (75 g). The resultant oil (547 g) was distilled under vacuum to give 3 main fractions:

| | | w/w yields |
|---|---|---|
| Butene dimers b.p | 38–40°/11 mm Hg | 10% |
| Indanes and precursors b.p. | 70–100°/6 mm Hg | 63% |
| -methyl sytrene dimers b.p. | 114–140°/2 mm Hg | 19% |

G.L.C. analysis (9–10% SP 2100 at 180° C.) of the second fraction gave the following individual yields of components:

| | |
|---|---|
| 1,1,2,3,3-penta methylindane | 55.5% |
| 1,1,3-trimethyl-3-ethyl indane | 4.0% |
| Indane precursors | 3.5% |

[1] 99% pure by GLC supplied by the Koch-Light Company
[2] as supplied by Shell (Holland)
[3] SLR grade (S.G 1.75) as supplied by the Fisons Company Ltd.

EXAMPLE 2

A mixture of -methyl styrene (349 g) and commercial grade 2-methylbut-2-ene as used in Example 1 (207 g) was added over 3.75 hour to the acid recovered from Example 1 (511 g) at 25°–27° C. Stirring was continued for a further 2 hours. The organic layer was separated, washed and distilled as in Example 1 to give a 63.5% w/w yield of indanes and precursors.

EXAMPLE 3

Example of multiple Recycle of Phosphoric Acid

A mixture of -methylstyrene (236 g) and commercial grade 2-methylbutene-2, as used in Example 1, (140 g) was added over 4 hours to 90% w/w ortho phosphoric acid (346 g) at 25°–30° C. Stirring was continued for a further 2 hours. After the two phases had separated out 95% by volume of the top (organic) phase was sucked off and washed separately (as in Example 1). A fresh mixture of α methylstyrene (236 g) and 2-methylbutene-2 (140 g) was then added to the same phosphoric acid under identical conditions used for the first batch. This oil was sucked off and washed and a further six charges of mixed reagent feed were added to the phosphoric acid. At the end of the eighth batch 345 g of orthophosphoric acid was recovered. (99.7% recovery).

The washed oil phases were combined to give 2948 g of crude product which was distilled as in Example 1. 1950 g of indanes and precursors (b.p. 70°–110°/6 mm Hg) or 64% w/w yield were recovered.

We claim:

1. A process for the production of an indane of the formula:

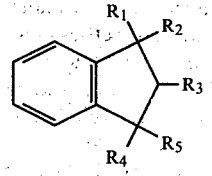

wherein $R_3$ represents a hydrogen atom or a methyl group; at least one of $R_1$ and $R_2$ represents a methyl group and the other represents a hydrogen atom or a methyl group; and $R_4$ and $R_5$ which may be the same or different represent alkyl groups having from 1 to 3 carbon atoms, which comprises; reacting a styrene with an alkene in the presence of an acid catalyst to form a reaction product mixture containing said indane, characterised in that the styrene is a compound of the formula:

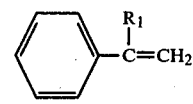

wherein $R_1$ represents a hydrogen atom or a methyl group; the alkene is selected from the group consisting of propylene, 2-methyl-but-1-ene, 2-methyl-but-2-ene, 2-methyl-pent-1-ene, 2-methyl-pent-2-ene, 3-methyl-but-1-ene, isobutylene and diisobutylene, and the acid catalyst consists essentially of an aqueous solution of phosphoric acid which comprises above 85% w/w phosphoric acid.

2. The process according to claim 1, wherein the catalyst is an aqueous solution of phosphoric acid which comprises at least 88% w/w phosphoric acid.

3. A process according to claim 2, in which the concentration is 88 to 95% by weight.

4. A process according to claim 2, in which the concentration is from 88 to 92% by weight.

5. A process according to claim 2, in which the styrene is α-methylstyrene and the alkene is selected from the group consisting of 2-methyl-but-1ene, 2-methyl-but-1-ene and isobutylene.

6. A process according to claim 2, in which the amount of phosphoric acid is from 1 to 5 mols per mol styrene.

7. A process according to claim 2 in which the amount of phosphoric acid is from 1.25 to 2 mols per mol styrene.

8. A process for the production of an indane comprising reacting α-methylstyrene with an alkene selected from the group comprising 2-methyl-but-1-ene and 2-methyl-but-2-ene in the presence of an acid catalyst that consists essentially of phosphoric acid and in which the phosphoric acid is present as an aqueous solution having a concentration of phosphoric acid greater than 85% by weight.

9. A process according to claim 8, in which the alkene is 2-methyl-but-2-ene.

10. A process according to claim 8, in which the concentration of phosphoric acid is at least 88%.

11. A process according to claim 8, in which the concentration of phosphoric acid is from 88 to 95%.

12. A process according to claim 8, in which the concentration of phosphoric acid is from 88 to 92%.

13. A process according to claim 8, in which the reaction product mixture settles into an organic layer containing the indane and an acid layer containing the acid catalyst, the layers are separated and the acid layer is re-used as the acid catalyst in a subsequent reaction of the styrene with the alkene.

14. A process for the production of an indane of the formula:

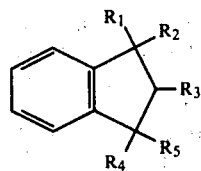

wherein $R_3$ represents a hydrogen atom or a methyl group; at least one of $R_1$ and $R_2$ represents a methyl group and the other represents a hydrogen atom or a methyl group; and $R_4$ and $R_5$ which may the same or different represent alkyl groups having from 1 to 3 carbon atoms, which comprises; reacting a styrene with an alkene in the presence of an acid catalyst to form a reaction product mixture containing said indane, characterised in that the styrene is a compound of the formula:

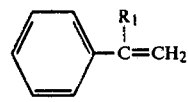

wherein $R_1$ represents a hydrogen atom or a methyl group; the alkene is selected from the group consisting of propylene, 2-methyl-but-1-ene, 2-methyl-but-2-ene, 2-methyl-pent-1-ene, 2-methyl-pent-2-ene, 3-methyl-but-1-ene, isobutylene and diisobutylene, and the acid catalyst consists essentially of an aqueous solution of phosphoric acid and the concentration of the phosphoric acid in the solution is above 85% by weight, and the reaction product mixture settles into an organic layer containing the indane and an acid layer containing the acid catalyst, the layers are separated and the acid layer is re-used as the acid catalyst in a subsequent reaction of the styrene with the alkene.

15. A process according to claim 14, in which the concentration of phosphoric acid is at least 88%.

16. A process according to claim 14, in which the concentration of phosphoric acid is from 88 to 95% by weight.

17. A process according to claim 14, in which the concentration of phosphoric acid is from 88 to 92%.

* * * * *